US008916109B2

(12) United States Patent
Okada et al.

(10) Patent No.: US 8,916,109 B2
(45) Date of Patent: Dec. 23, 2014

(54) DIAGNOSIS SUPPORT METHOD, DIAGNOSIS SUPPORT SYSTEM, AND DIAGNOSIS SUPPORT APPARATUS

(75) Inventors: Seiki Okada, Kobe (JP); Toshiyuki Sato, Kobe (JP)

(73) Assignee: Sysmex Corporation, Hyogo (JP)

( * ) Notice: Subject to any disclaimer, the term of this patent is extended or adjusted under 35 U.S.C. 154(b) by 309 days.

(21) Appl. No.: 13/072,076

(22) Filed: Mar. 25, 2011

(65) Prior Publication Data
US 2011/0237919 A1 Sep. 29, 2011

(30) Foreign Application Priority Data
Mar. 26, 2010 (JP) ................ 2010-072522

(51) Int. Cl.
*G01N 33/00* (2006.01)
*A61B 5/145* (2006.01)
(52) U.S. Cl.
CPC .......... *A61B 5/14532* (2013.01); *A61B 5/14514* (2013.01)
USPC ........... 422/404; 422/68.1; 422/402; 422/403
(58) Field of Classification Search
USPC ................. 422/68.1, 402, 403, 404
See application file for complete search history.

(56) References Cited

U.S. PATENT DOCUMENTS

| 6,424,847 | B1 | 7/2002 | Mastrototaro et al. |
| 2004/0260324 | A1 | 12/2004 | Fukuzawa et al. |
| 2007/0213657 | A1 | 9/2007 | Jennewine et al. |
| 2008/0004601 | A1* | 1/2008 | Jennewine et al. ........ 604/890.1 |
| 2011/0124998 | A1 | 5/2011 | Okada |

FOREIGN PATENT DOCUMENTS

| WO | 02/15777 A1 | 2/2002 |
| WO | 2007/101260 A2 | 9/2007 |
| WO | 2010/013808 A1 | 2/2010 |

OTHER PUBLICATIONS

Hoi-Hansen T et al; "The Somogyi phenomenon revisited using continuous glucose monitoring in daily life", Diabetologia; Clinical and Experimental Diabetes and Metabolism, Springer, Berlin, DE, vol. 48, No. 11, Nov. 1, 2005, pp. 2437-2438; XP019322373.

* cited by examiner

*Primary Examiner* — Sam P Siefke
(74) *Attorney, Agent, or Firm* — Sughrue Mion, PLLC

(57) ABSTRACT

A diagnosis support method comprising: obtaining first blood glucose level information at a first time point and/or second blood glucose level information at a second time point which is later, by a predetermined period, than the first time point; placing a collection member, which is configured to collect a tissue fluid, on the skin of the subject for the predetermined period from the first time point to the second time point; obtaining glucose information about an amount of glucose contained in the tissue fluid collected by the collection member; and generating diagnosis support information for supporting a diagnosis of presence or absence of hypoglycemia in the subject, based on the first blood glucose level information and/or the second blood glucose level information and the glucose information. A diagnosis support system and a diagnosis support apparatus are also disclosed.

14 Claims, 16 Drawing Sheets

F I G. 5
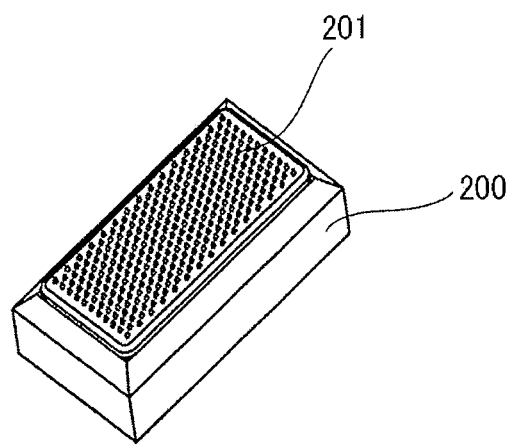

A+B : BLOOD GLUCOSE AUC OBTAINED FROM BLOOD GLUCOSE
      LEVEL MEASURED BEFORE SLEEP AND BLOOD GLUCOSE
      LEVEL MEASURED AT WAKE UP (AUC1)

B : ACTUAL BLOOD GLUCOSE AUC (AUC2)

F I G. 1 6
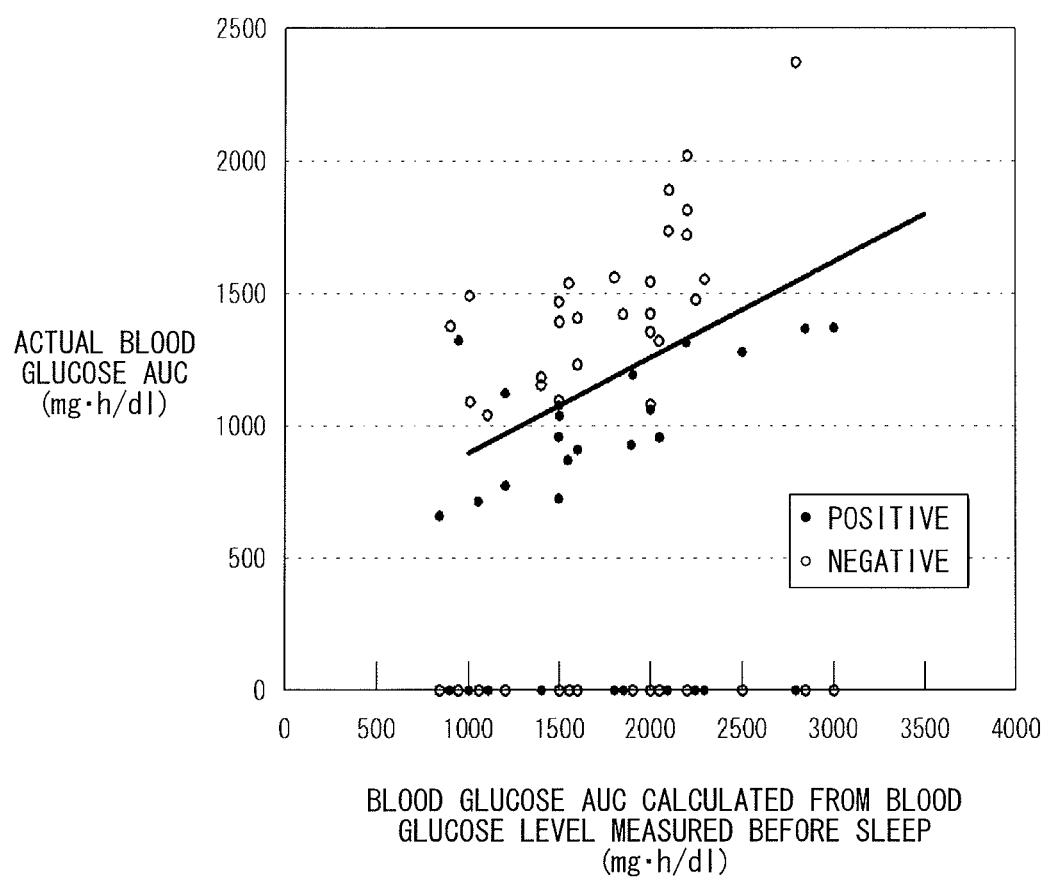

DIAGNOSIS SUPPORT METHOD, DIAGNOSIS SUPPORT SYSTEM, AND DIAGNOSIS SUPPORT APPARATUS

FIELD OF THE INVENTION

The present invention relates to a diagnosis support method, a diagnosis support system, and a diagnosis support apparatus.

BACKGROUND

Diabetic patients may fall into hypoglycemia during sleep (i.e., an episode of nocturnal hypoglycemia) (the term "hypoglycemia" generally refers to a state where the patient's blood glucose level drops to a level not higher than 70 mg/dl). For the purpose of making a diagnosis of the presence or absence of nocturnal hypoglycemia, a puncture device such as one disclosed in U.S. Patent Application Publication No. 2004-0260324 is used to puncture the skin of a subject to collect blood and measure the blood glucose level at night.

However, making a diagnosis of the presence or absence of nocturnal hypoglycemia in such a manner is based on a blood glucose level measured only at one time point during the night. For this reason, the diagnosis result is not fully reliable. Moreover, the subject is required to wake up at night for the collection of blood. This disturbs the subject's sleep.

As a solution to the above problems, it is proposed to make continuous diagnoses of the presence or absence of nocturnal hypoglycemia by using a device for continuously measuring glucose concentrations. For example, International Publication WO2002/015777 discloses a device including: electrodes through which a current is applied to the skin of a subject to cause electroosmosis of glucose in the subject's body; a biosensor for reacting with the glucose which electroosmotically moves from the skin and outputting a signal accordingly; and a microprocessor for reading a glucose concentration every twenty minutes from the outputted signal and storing the glucose concentration.

U.S. Pat. No. 6,424,847 discloses a glucose monitor system including: a glucose sensor to be inserted into subcutaneous tissue of a subject; and a glucose monitor for obtaining a signal from the glucose sensor at predetermined intervals, thereby measuring glucose concentrations in the subcutaneous tissue.

Unlike the method disclosed by U.S. Patent Application Publication No. 2004-0260324, the use of the device disclosed in International Publication WO2002/015777 or the system disclosed in U.S. Pat. No. 6,424,847 allows blood glucose levels of the subject to be obtained continuously. This improves the accuracy in diagnosis of the presence or absence of hypoglycemia.

However, the device disclosed in International Publication WO2002/015777, which includes the electrodes and the biosensor, needs to be worn on an arm of a subject. Also, the system disclosed in U.S. Pat. No. 6,424,847 requires the glucose sensor to be kept inserted in the skin of a subject. Thus, the subject has a burden of wearing a device if the method using the device of International Publication WO2002/015777 or the method using the system of U.S. Pat. No. 6,424,847 is employed. In particular, wearing such a device during sleep is a significant burden for the subject.

SUMMARY

The scope of the present invention is defined solely by the appended claims, and is not affected to any degree by the statements within this summary.

A first aspect of the present invention is a diagnosis support method comprising: obtaining first blood glucose level information about a blood glucose level of a subject at a first time point and/or second blood glucose level information about a blood glucose level of the subject at a second time point which is later, by a predetermined period, than the first time point; placing a collection member, which is configured to collect a tissue fluid, on the skin of the subject for the predetermined period from the first time point to the second time point; obtaining glucose information about an amount of glucose contained in the tissue fluid collected by the collection member which is placed on the skin of the subject for the predetermined period; and generating diagnosis support information for supporting a diagnosis of presence or absence of hypoglycemia in the subject, based on the first blood glucose level information and/or the second blood glucose level information and the glucose information.

A second aspect of the present invention is a diagnosis support system comprising: a collection member configured to collect a tissue fluid from a subject; an information obtaining section for obtaining glucose information about an amount of glucose contained in the tissue fluid collected by the collection member which is placed on the skin of the subject for a predetermined period from a first time point to a second time point; and an analysis section for generating diagnosis support information for supporting a diagnosis of presence or absence of hypoglycemia in the subject, based on first blood glucose level information about the blood glucose level of the subject at the first time point and/or second blood glucose level information about the blood glucose level of the subject at the second time point and the glucose information.

A third aspect of the present invention is a diagnosis support apparatus comprising: an obtaining section for obtaining glucose information about an amount of glucose contained in a tissue fluid collected by a collection member which is placed on a skin of a subject for a predetermined period from a first time point to a second time point; and an analysis section for generating diagnosis support information for supporting a diagnosis of presence or absence of hypoglycemia in the subject, based on first blood glucose level information about the blood glucose level of the subject at a first time point and/or second blood glucose level information about the blood glucose level of the subject at a second time point and the glucose information.

BRIEF DESCRIPTION OF THE DRAWINGS

FIG. 5 is a perspective view of a microneedle chip attached to the micropore forming device shown in FIG. 4;

FIG. 16 shows an example of screening where a single blood glucose level measured before bedtime is used.

DETAILED DESCRIPTION OF THE EMBODIMENT

[Diagnosis Support System]

Figure 1:
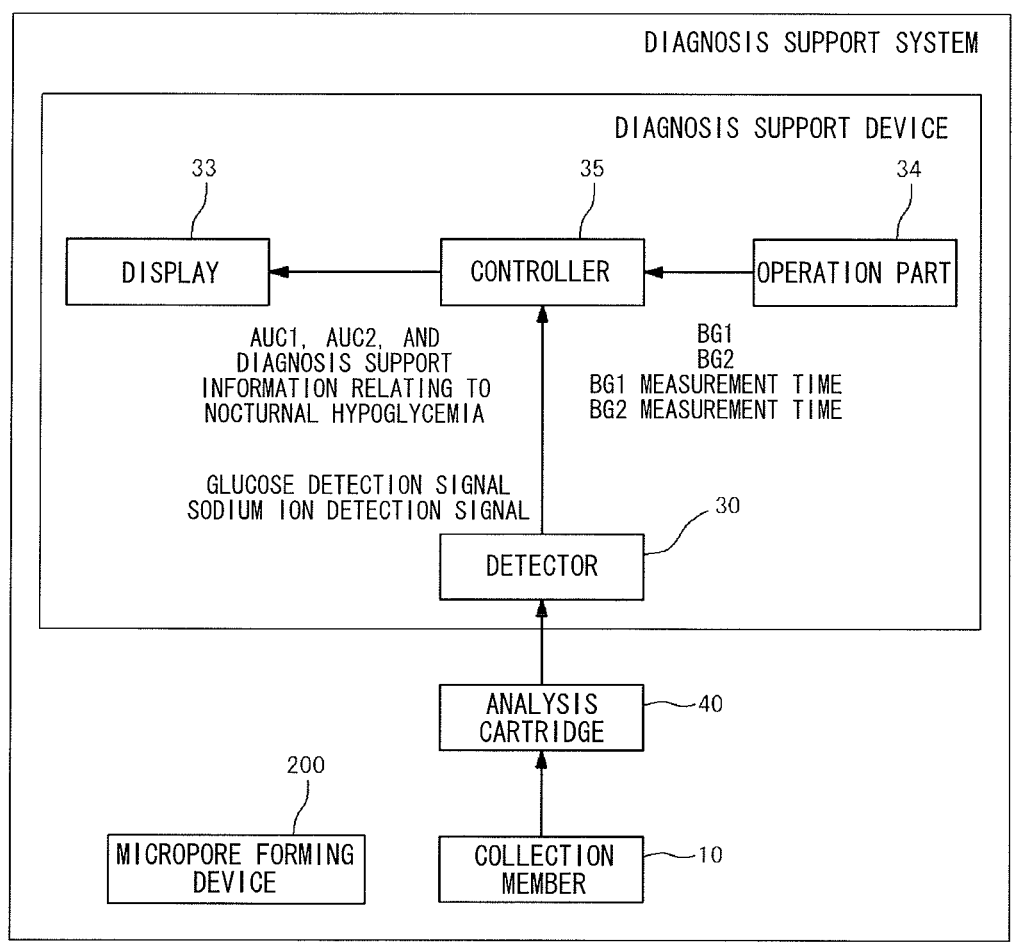
FIG. 1 is a block diagram showing an overall configuration of a diagnosis support system according to an embodiment of the present invention.

FIG. 1 is a block diagram showing an overall configuration of a diagnosis support system according to an embodiment of the present invention.

Nocturnal hypoglycemia is one of the symptoms often experienced by diabetic patients who are receiving treatment with medications such as insulin. If the dosage of medication administered to a diabetic patient is excessive, or if the administered medication shows excessive efficacy, the blood glucose level of the patient may drop excessively during sleep. As a result, the patient may fall into hypoglycemia. When falling into nocturnal hypoglycemia, the patient may wake up or experience numbness in his/her limbs during the night. Therefore, for a patient suspected of having nocturnal hypoglycemia, it is necessary to reduce the dosage of medications administered to the patient, or switch the administered medications to less effective ones, based on the attending doctor's diagnosis. The diagnosis support system of the present invention provides information as to whether the probability of a subject having had nocturnal hypoglycemia is high or not, and thus helps doctors to make a diagnosis.

The term "hypoglycemia" used herein refers to a state where the blood glucose level of a subject is below a predetermined value. In the embodiment described below, the term "hypoglycemia" refers to a state where the blood glucose level is below 70 mg/d1. However, the predetermined value is not limited to 70 mg/d1 but may be set to any appropriate value.

The main components of the diagnosis support system include: a micropore forming device 200 for forming micropores in the skin of a subject; a collection member 10 configured to collect a tissue fluid extracted from the skin in which the micropores are formed; and a diagnosis support apparatus 20. The diagnosis support apparatus 20 includes a detector 30, an operation part 34, a controller 35, and a display 33. The detector 30 detects glucose and sodium ion that are contained in the tissue fluid collected by the collection member 10, and outputs detection signals, accordingly. The operation part 34 is provided for allowing inputting of blood glucose level information BG1 and blood glucose level information BG2 which are obtained through Self-Monitoring of Blood Glucose (SMBG) and inputting of a measurement time t1 and a measurement time t2 at which the blood glucose level information BG1 and the blood glucose level information BG2 have been obtained, respectively. Based on the detection signals outputted from the detector 30, the controller 35 obtains a glucose concentration and sodium ion concentration in the tissue fluid collected by the collection member 10. Further, based on the blood glucose level information BG1 and BG2 and the measurement times t1 and t2 inputted via the operation part 34, the controller 35 calculates a first area under the blood glucose-time curve (AUC1). Moreover, the controller 35 calculates a second area under the blood glucose-time curve (AUC2) based on the obtained glucose concentration and sodium ion concentration. Based on the calculated AUC1 and AUC2, the controller 35 generates diagnosis support information as to whether the subject has had nocturnal hypoglycemia, and controls the display 33 to display the diagnosis support information.

[Diagnosis Support Apparatus]

Figure 2:
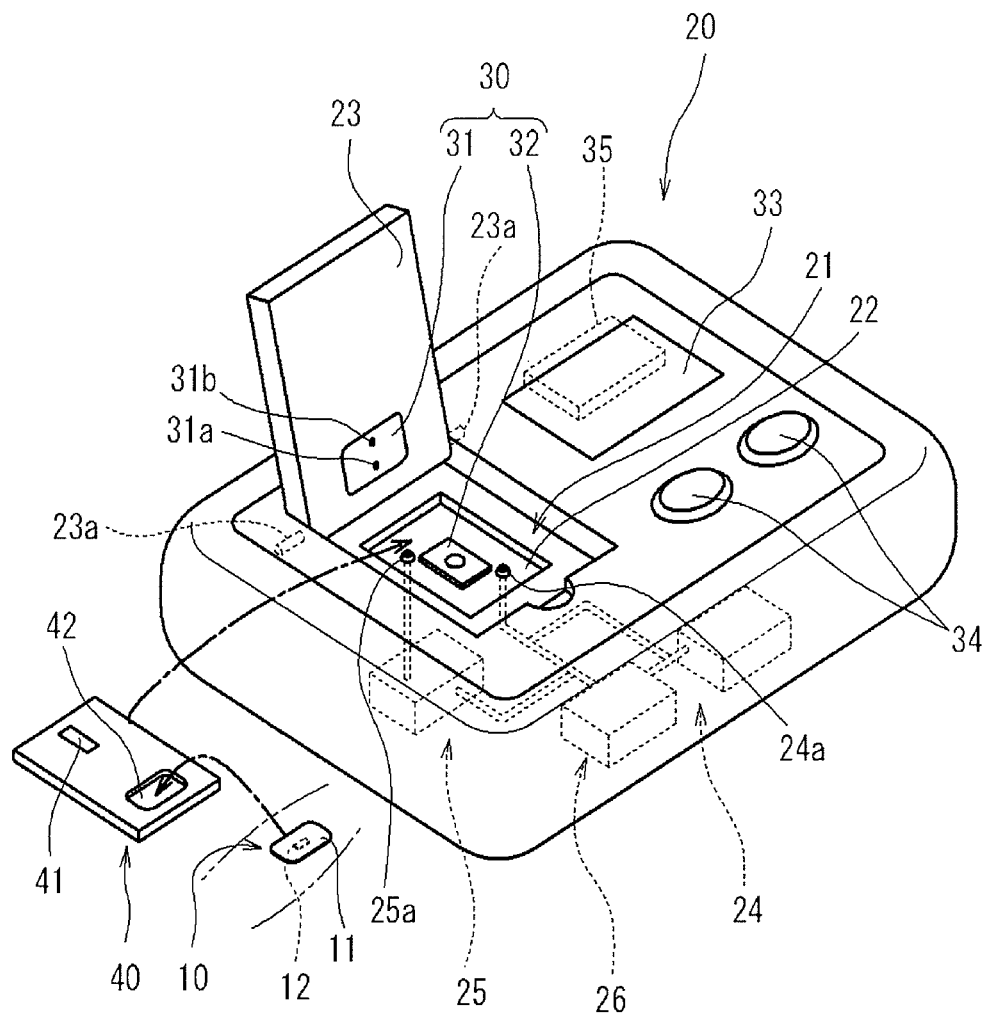
FIG. 2 is a perspective view illustrating an external view of a diagnosis support apparatus according to the embodiment of the present invention.

FIG. 2 is a perspective view illustrating an external view of the diagnosis support apparatus 20 according to the embodiment of the present invention. The diagnosis support apparatus 20 obtains the glucose concentration and the sodium ion concentration in the tissue fluid collected by a collector 12 of the collection member 10, and, based on the obtained glucose concentration and sodium ion concentration as well as a blood glucose level that is separately measured, generates diagnosis support information for supporting a diagnosis of the presence or absence of hypoglycemia in the subject. The diagnosis support apparatus 20 includes: the detector 30; the controller 35 including an obtaining section and an analysis section; the display 33 for displaying the diagnosis support information; and operation buttons 34 which act as an operation part via which a measurement start instruction or the like is given.

The diagnosis support apparatus 20 includes a thick parallelepiped casing. A recess 21 is formed in the top face of the casing. A cartridge placement part 22, which is a recess, is formed in the recess 21 to reach a deeper point than the recess 21. The recess 21 is connected to a movable top board 23 whose thickness is substantially the same as the height of the side walls of the recess 21. The movable top board 23 in a state as shown in FIG. 2 can be accommodated in the recess 21 by being folded (i.e., pivoted) with respect to a support shaft 23a. Similarly, the movable top board 23 in a state of being accommodated in the recess 21 can be caused to stand as shown in FIG. 2 by being pivoted with respect to the support shaft 23a. The cartridge placement part 22 has such a size as to be able to accommodate an analysis cartridge 40, which will be described below.

The movable top board 23 is supported by the support shaft in such a manner as to be urged in the direction of, and thereby accommodated into, the recess 21. Accordingly, the analysis cartridge 40 is, when placed at the cartridge placement part 22, pushed by the movable top board 23 from above.

The detector 30 detects components contained in the tissue fluid (i.e., a sample) collected by the collector 12. The detector 30 includes a glucose detector 31 and a sodium ion detector 32.

The glucose detector 31 is provided at the back face of the movable top board 23, that is, at the face that is opposed to the cartridge placement part 22 when the movable top board 23 is in a state of being accommodated in the recess 21. The glucose detector 31 includes a light source 31a for emitting light and a light receiver 31b for receiving reflected light generated from the light emitted from the light source 31a. That is, the glucose detector 31 is configured to emit light to the analysis cartridge 40 placed at the cartridge placement part 22, and to receive the light reflected by the analysis cartridge 40.

The sodium ion detector 32 is provided at the bottom face of the cartridge placement part 22. The sodium ion detector 32 includes a rectangular plate-shaped member provided at the bottom face of the cartridge placement part 22. A pair of sodium ion concentration measurement electrodes is provided substantially at the center of the plate-shaped member. The sodium ion concentration measurement electrodes include: a sodium ion selective electrode which is formed from silver/silver chloride and which includes a sodium ion selective membrane; and a silver/silver chloride electrode which is a counter electrode.

The controller 35 is provided within the diagnosis support apparatus 20. The controller 35 includes a CPU as an analysis section and a ROM, RAM, and the like as a memory section. The CPU loads and executes a program stored in the ROM, thereby controlling the operations of the respective components of the diagnosis support apparatus 20. The RAM is used as an area where the program stored in the ROM is loaded at the time of execution of the program.

The diagnosis support apparatus 20 includes: a supply part 24 which includes a pump; a tank 26 for storing a collection fluid which is pure water used for collecting the tissue fluid collected by the collector 12; and a waste fluid tank 25 for storing a waste fluid. The supply part 24 sends air into the tank 26 and thereby injects, through a nipple 24a, the collection fluid stored in the tank 26 into the analysis cartridge 40 placed at the cartridge placement part 22.

The waste fluid tank 25 is a mechanism into which the pure water sent by the supply part 24 to the analysis cartridge 40 is discharged. The waste fluid tank 25 stores a fluid that is discharged thereinto through a nipple 25a.

Figure 3:
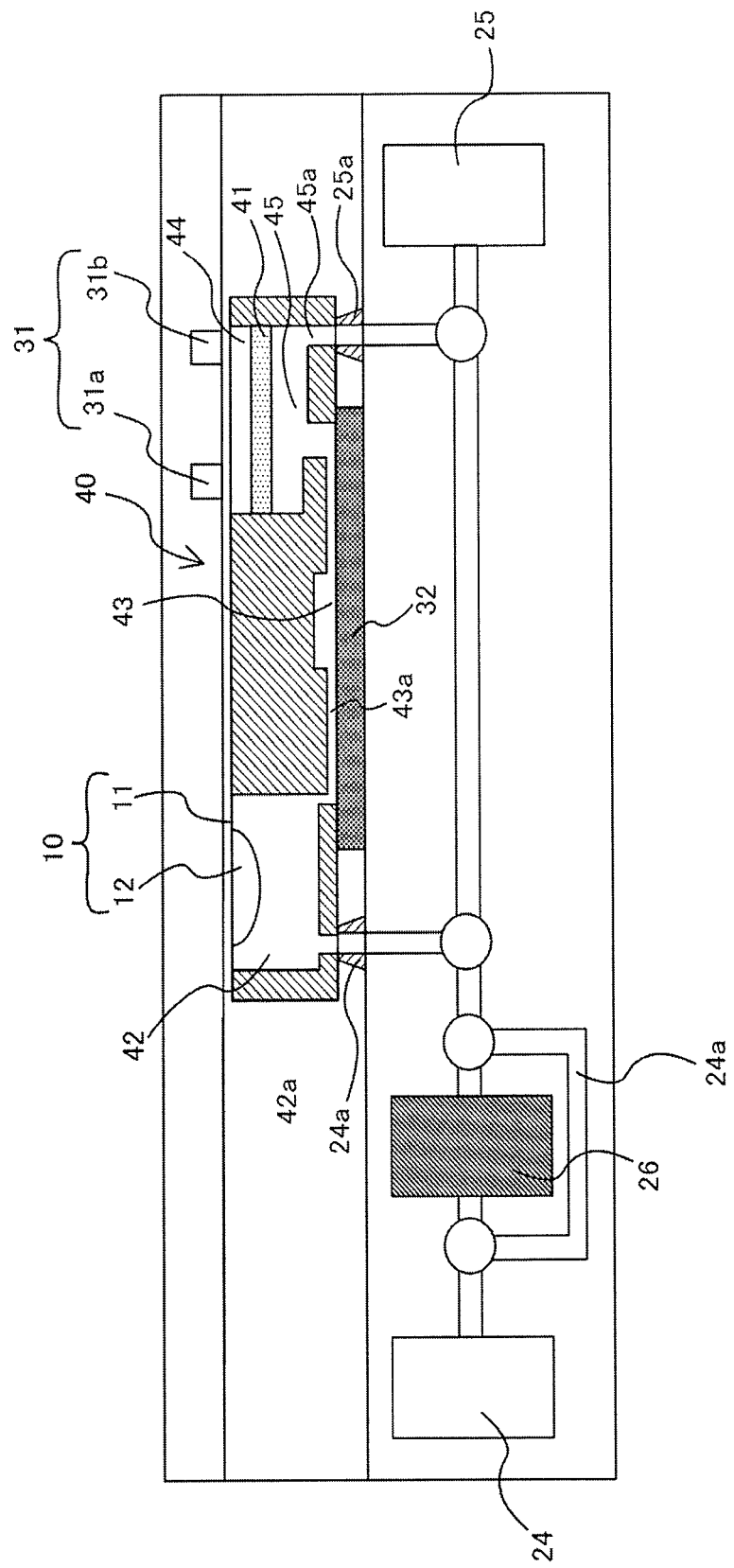
FIG. 3 is a schematic cross-sectional view showing a state where an analysis cartridge is placed at a cartridge placement part.

FIG. 3 is a schematic cross-sectional view showing a state where the analysis cartridge 40 is placed at the cartridge placement part 22. First, the structure of the analysis cartridge 40 is described with reference to FIG. 3.

The main components of the analysis cartridge 40 include a gel storing part 42, a glucose reactant 41, and an optical waveguide member 44. The gel storing part 42 is formed as a recess in the upper face of the analysis cartridge 40. The gel storing part 42 has an injection hole 42a formed at its bottom. The injection hole 42a communicates with the nipple 24a provided at the cartridge placement part 22. A groove that communicates with the gel storing part 42 is formed in the lower face of the analysis cartridge 40. The groove and the sodium ion detector 32 provided at the bottom of the cartridge placement part 22 form a flow path 43a. A part of the flow path 43a acts as a first reservoir 43 where the sodium ion detector 32 detects a sodium ion concentration. The downstream of the flow path 43a communicates with a second reservoir 45. The second reservoir 45 is formed as a recess in the upper face of the analysis cartridge 40, and the opening of the recess is sealed with the optical waveguide member 44 which includes an optical waveguide. The glucose reactant 41, which reacts with glucose and thereby changes its color, is provided at the lower face of the optical waveguide member 44. A discharging hole 45a, which communicates with the nipple 25a provided at the cartridge placement part 22, is provided at the bottom of the second reservoir 45.

The diagnosis support apparatus 20 measures the glucose and sodium ion concentrations in the tissue fluid that is collected by the collection member 10 in a manner as described below. First, the collection member 10, which has been adhered to the skin of a subject as indicated by dashed-dotted lines in FIG. 2 for a predetermined period, is removed from the skin. Then, the collection member 10 is adhered to the gel storing part 42 of the analysis cartridge 40. The analysis cartridge 40 is placed at the cartridge placement part 22 of the diagnosis support apparatus 20, and then the movable top board 23 is closed.

When a measurement start instruction is given via the operation buttons 34, the supply part 24 supplies air to the tank 26. Accordingly, the collection fluid is sent from the tank 26 to the nipple 24a, and injected into the gel storing part 42 through the injection hole 42a. Consequently, the gel storing part 42 is filled with the collection fluid. When the gel storing part 42 is kept filled with the collection fluid for a predetermined period, the tissue fluid collected by the collector 12 is dispersed into the collection fluid. After the predetermined period has elapsed, the supply part 24 sends air into the gel storing part 42 through a bypass 24a. As a result, the fluid within the gel storing part 42 is sent to the first reservoir 43 and the second reservoir 45 through the flow path 43a.

The sodium ion detector 32 applies a constant voltage to the fluid reserved in the first reservoir 43 via the sodium ion concentration measurement electrodes. A current value obtained at this time is proportionate to the sodium ion concentration in the fluid. The sodium ion detector 32 outputs the obtained current value as a detection signal to the controller 35. The controller 35 obtains a sodium ion concentration based on the current value contained in the detection signal and a calibration curve that is stored in advance in the memory section of the controller 35.

In the second reservoir 45, glucose in the collection fluid reacts with the glucose reactant 41. As a result, the color of the glucose reactant 41 changes. The glucose detector 31 emits light from the light source 31a to the optical waveguide member 44. The light is then outputted from the optical waveguide member 44 and received by the light receiver 31b. The light emitted from the light source 31a travels while being absorbed by the discolored glucose reactant 41 and being repeatedly reflected within the optical waveguide member 44. Then, the light falls on the light receiver 31b. Accordingly, the amount of light received by the light receiver 31b is proportionate to the degree of discoloration of the glucose reactant 41, that is, proportionate to the amount of glucose in the collection fluid. The glucose detector 31 outputs the obtained amount of received light as a detection signal to the controller 35. The controller 35 obtains a glucose concentration based on the amount of received light contained in the detection signal and a calibration curve that is stored in advance in the memory section of the controller 35.

When the sodium ion concentration and the glucose concentration are obtained, additional air is sent into the analysis cartridge 40 from the supply part 24. As a result, the collection fluid is sent into the waste fluid tank 25 through the discharging hole 45a and the nipple 25a. This is the end of the series of steps of the measurement.

[Micropore Forming Device]

Described next is an example of a micropore forming device for forming micropores in the skin of the subject. The micropore forming device forms a large number of micropores in the skin of the subject, thereby prompting the extraction of the tissue fluid from the skin of the subject.

Figure 4:
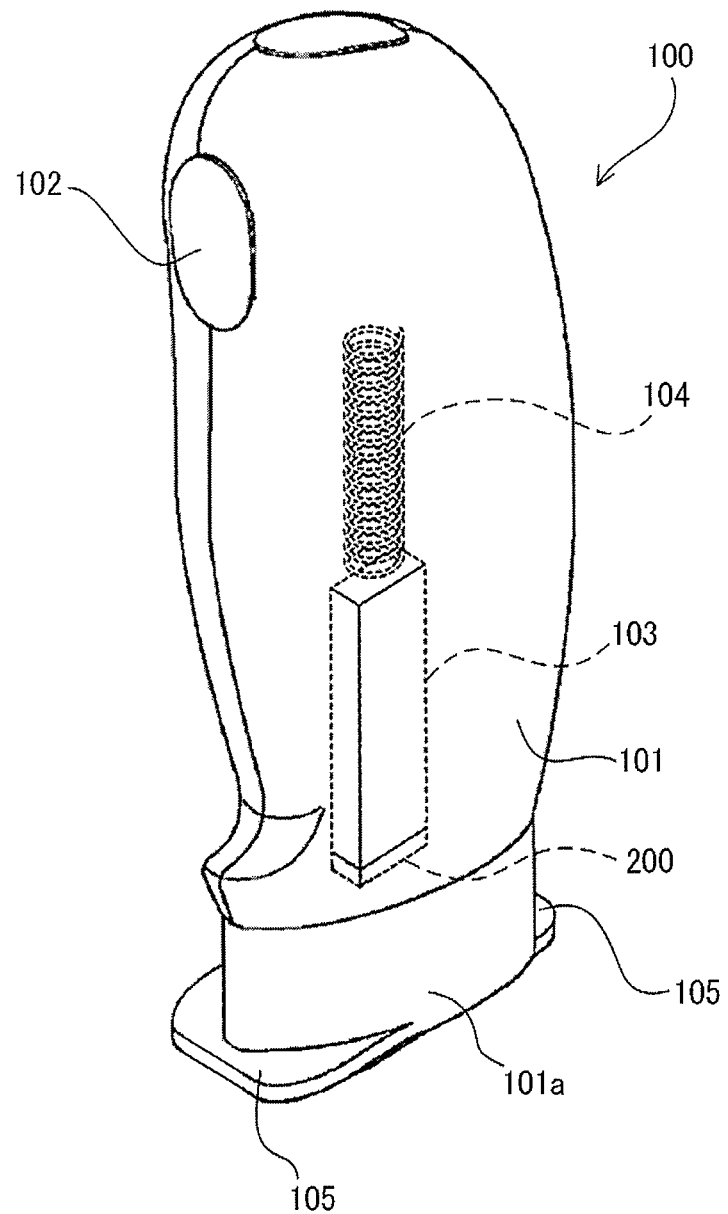
FIG. 4 is a perspective view illustrating an example of a micropore forming device of the diagnosis support system of the present invention.
Figure 6:
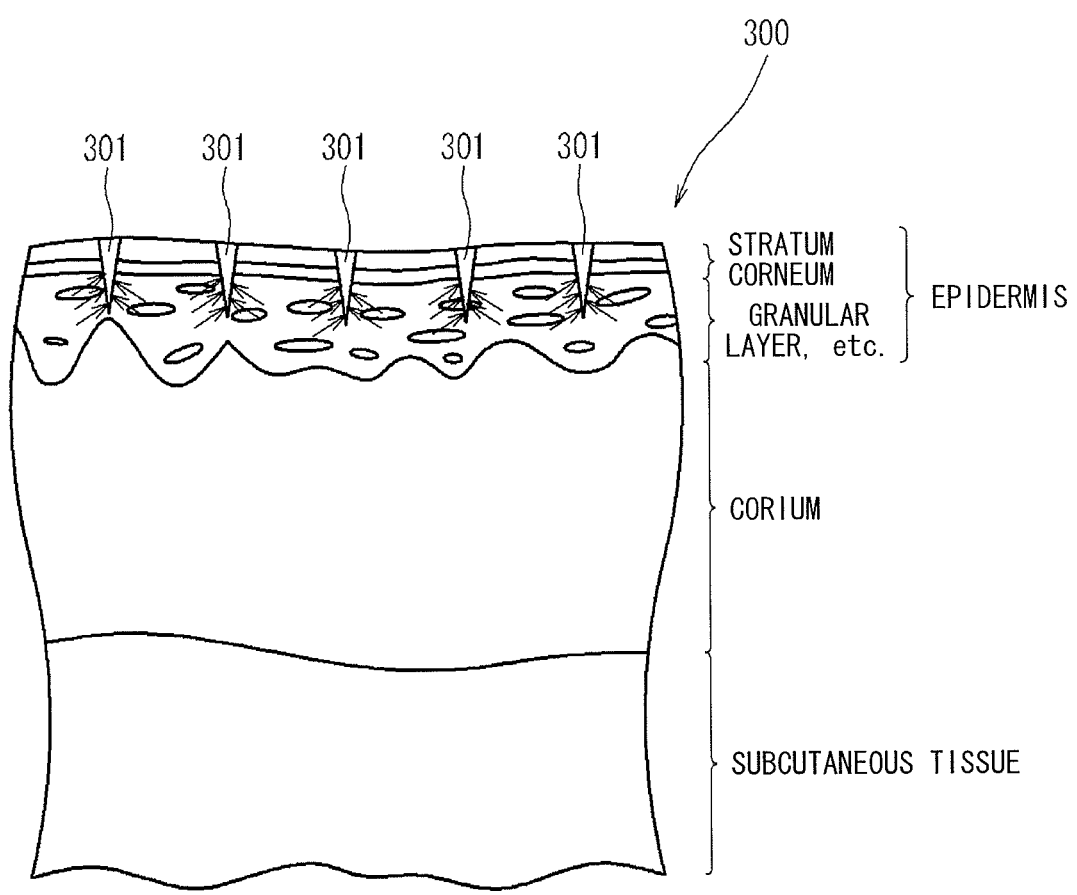
FIG. 6 illustrates a cross section of skin in which micropores are formed by the micropore forming device.

FIG. 4 is a perspective view illustrating a puncture device 100 according to an example of the micropore forming device of the diagnosis support system of the present invention. FIG. 5 is a perspective view of a microneedle chip 200 attached to the puncture device 100 shown in FIG. 4. FIG. 6 illustrates a cross section of the skin in which micropores are formed by the puncture device 100.

As shown in FIG. 4 to FIG. 6, the microneedle chip 200, which is sterilized, is attached to the puncture device 100. The puncture device 100 forms tissue fluid extraction holes (micropores 301) in skin 300 of the subject by causing microneedles 201 of the microneedle chip 200 to come into contact with the epidermis of a living body (i.e., the skin 300 of the subject).

As shown in FIG. 4, the puncture device 100 includes a casing 101, a release button 102 provided at the surface of the casing 101, an array chuck 103 and a spring member 104 which are provided within the casing 101, and a flange 105 which is formed at a bottom part 101a of the casing 101. An opening (not shown) is formed in the lower end face of the bottom part 101a of the casing 101 (i.e., the face to come into contact with the skin). The opening allows the microneedle chip 200 to pass therethrough. The spring member 104 has a function of urging the array chuck 103 in the direction of the lower end face. The array chuck 103 is configured such that the microneedle chip 200 is attachable to the lower end of the array chuck 103. Multiple microneedles 201 are formed on the lower face of the microneedle chip 200. The lower face of the microneedle chip 200 has a size of 10 mm (longer sides)×5 mm (shorter sides). The puncture device 100 includes a fixing mechanism for fixing the array chuck 103 in a state where the array chuck 103 is lifted upward (i.e., in a direction opposite to the puncturing direction) against the urging force of the spring member 104. When a user (i.e., the subject) presses the release button 102, the fixed state of the array chuck 103 by the fixing mechanism is canceled. Then, the urging force of the spring member 104 moves the array chuck 103. As a result, the microneedles 201 of the microneedle chip 200 projected out of the opening puncture the skin. In this manner, the micropores 301, which extend within the epidermis but do not reach the corium as shown in FIG. 6, are formed in the skin 300 of the subject.

[Collection Member]

Described next is the collection member 10 for collecting a tissue fluid from the skin of the subject. The collection member 10 is adhered to the skin of the subject for the purpose of collecting a tissue fluid from the skin of the subject. The collection member adhered to the skin is removed from the skin after a predetermined period has elapsed, and used in measurement performed by the diagnosis support apparatus.

Figure 7:
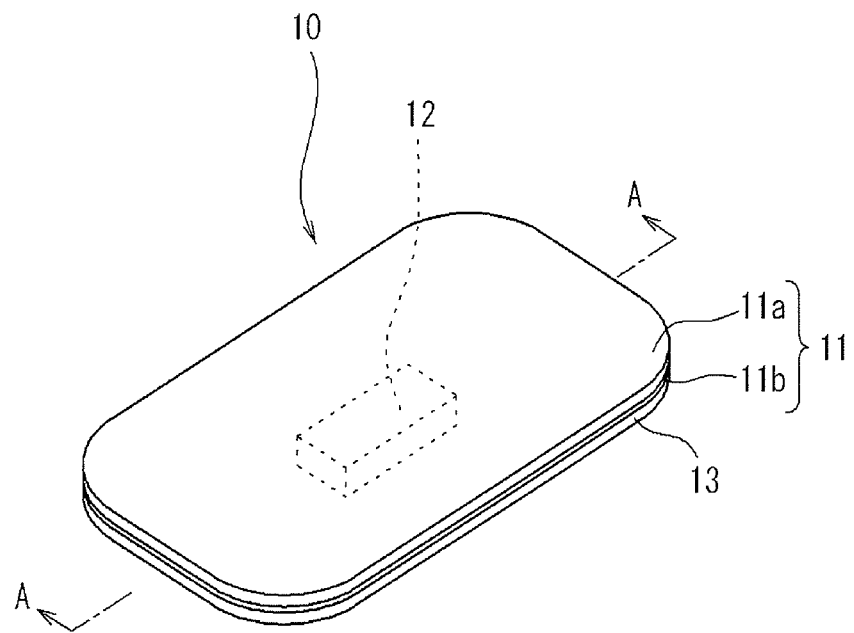
FIG. 7 is a perspective view illustrating an example of a collection member for use in a diagnosis support method of the present invention.
Figure 8:
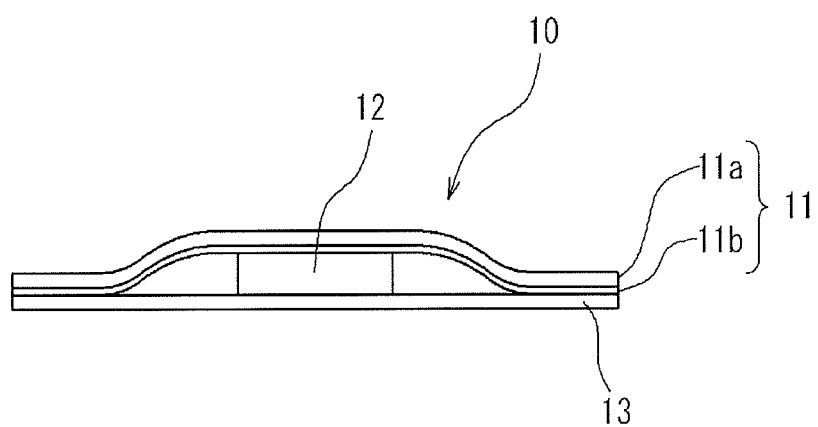
FIG. 8 is a cross-sectional view of FIG. 7 cut along a line A-A indicated in FIG. 7.

FIG. 7 is a perspective view illustrating the collection member 10 which includes a holding sheet 11 and the collector 12 held by the holding sheet 11. FIG. 8 is a cross-sectional view of FIG. 7 cut along a line A-A indicated in FIG. 7.

The collector 12 is formed of a gel having water retentivity for holding the tissue fluid extracted from the skin of the subject, and contains pure water as an extraction medium. The gel is not particularly limited to any specific one as long as it has a tissue fluid collection capability. Preferably, the gel is formed from at least one type of hydrophilic polymer selected from the group consisting of polyvinyl alcohol and polyvinylpyrrolidone. The hydrophilic polymer forming the gel may be polyvinyl alcohol alone, polyvinylpyrrolidone alone, or a mixture of polyvinyl alcohol and polyvinylpyrrolidone. More preferably, the gel is formed from polyvinyl alcohol alone or a mixture of polyvinyl alcohol and polyvinylpyrrolidone.

The gel may be formed by a method in which the hydrophilic polymer is cross-linked in an aqueous solution. Specifically, the gel may be formed by a method in which: a coating is formed on a base material by coating the base material with a hydrophilic polymer aqueous solution; and the hydrophilic polymer contained in the coating is cross-linked. Examples of a cross-linking method for the hydrophilic polymer include chemical cross-linking and irradiation cross-linking It is desired to employ irradiation cross-linking which reduces the chance of chemical substances being mixed into the gel as impurities.

In the example shown in FIG. 7 and FIG. 8, the collector 12 is in a parallelepiped shape and the face thereof to come into contact with the skin has a size of 7 mm×12 mm. However, the shape and size of the collector 12 are not limited thereto.

The holding sheet 11 includes an oval sheet body 11a and an adhesive layer 11b formed on one face of the sheet body 11a. The face on which the adhesive layer 11b is formed is an adhesive face. The collector 12 is disposed substantially at the center of a release sheet 13 which is oval and which also acts as a mount board. The holding sheet 11 is affixed to the release sheet 13 in such a manner as to cover the collector 12. The collector 12 is held by the holding sheet 11 via part of the adhesive face of the holding sheet 11. The area of the holding sheet 11 is designed such that the holding sheet 11 is large enough to cover the collector 12 for the purpose of preventing the collector 12 from drying at the time of collection of the tissue fluid. To be specific, air tightness between the skin and the holding sheet 11 can be maintained at the time of collection of the tissue fluid by covering the collector 12 with the holding sheet 11. Accordingly, evaporation of moisture contained in the collector 12 can be suppressed at the time of collection of the tissue fluid.

The sheet body 11a of the holding sheet 11 is a colorless transparent sheet body or a colored transparent sheet body. Accordingly, the collector 12 held by the holding sheet 11 can be readily viewed from the surface side of the sheet body 11a (i.e., viewed through the face that is opposite to the adhesive layer 11b. Preferably, the sheet body 11a is one with low moisture permeability for the purpose of preventing the tissue fluid from evaporating and the collector 12 from drying. Examples of the material of the sheet body 11a include a polyethylene film, a polypropylene film, a polyester film, and a polyurethane film. In particular, a polyethylene film or a polyester film is preferred. The thickness of the sheet body 11a is not particularly limited, but may be approximately 0.025 to 0.5 mm.

The collection member 10 is adhered to the skin 300 of the subject by means of the adhesive face of the holding sheet 11, such that the collector 12 is placed at a micropore forming area of the subject (i.e., an area, on the skin 300 of the subject, in which the multiple micropores 301 have been formed by the puncture device 100 for the purpose of prompting the extraction of the tissue fluid). Then, the collector 12, placed at the micropore forming area, is left for a predetermined period, for example, a period not shorter than 60 minutes, preferably, not shorter than 180 minutes. The tissue fluid that is extracted through the micropores is collected by the collector 12.

[Diagnosis Support Method]

Next, a diagnosis support method using the diagnosis support system will be described.

Figure 9:
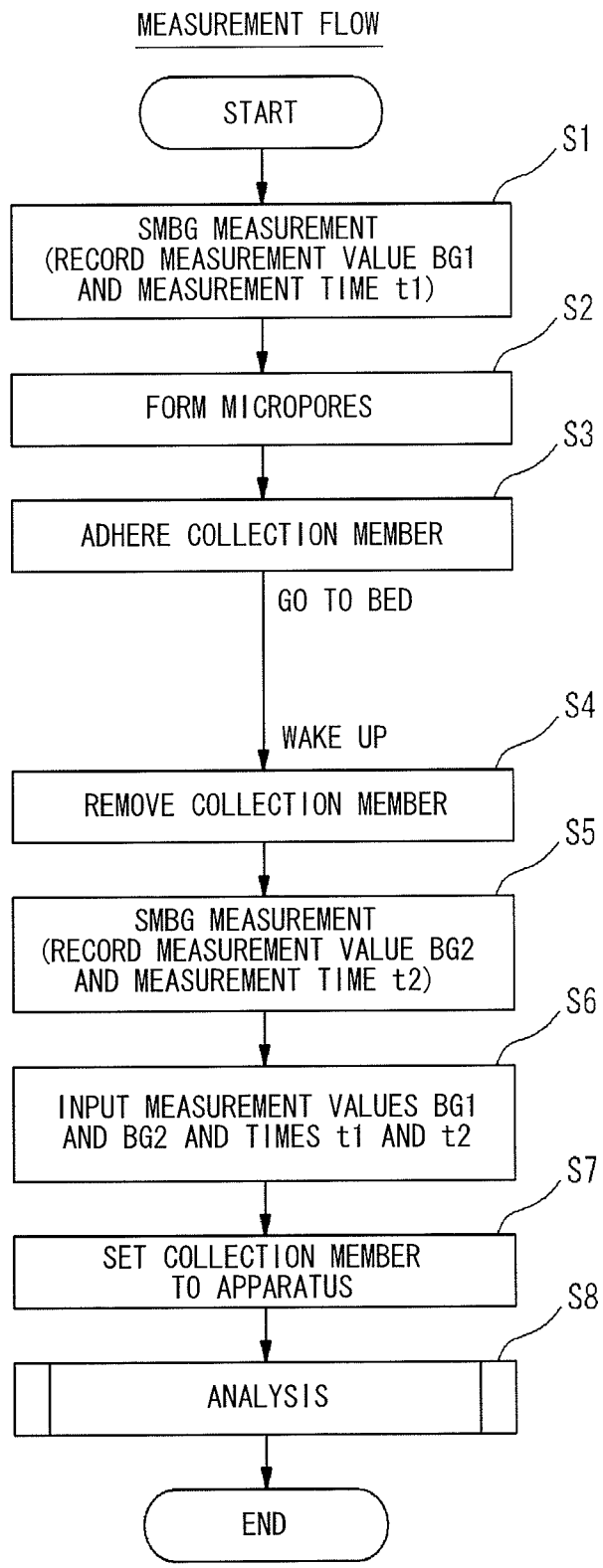
FIG. 9 is a flowchart showing a flow of the diagnosis support method of the present invention.

FIG. 9 is a flowchart showing a flow of the diagnosis support method of the present invention.

First, at step S1, the subject measures a blood glucose level by a suitable method at a first time point before going to bed (i.e., the measurement time t1), and records a measurement value BG1 (i.e., first blood glucose level information) and the measurement time t1.

A method for measuring the blood glucose level is not particularly limited but may be any method that allows the blood glucose level to be measured. Any publicly-known conventional method may be used for measuring the blood glucose level. It is preferred to use an SMBG (Self-Monitoring of Blood Glucose) device for measuring the blood glucose level since the SMBG device enables prompt measurement. Examples of commercial SMBG devices that can be used for measuring the blood glucose level include GLUTEST EVERY (available from SANWA KAGAKU KENKY-USHO), ONETOUCH ULTRA (available from Johnson&Johnson), NIPRO FreeStyle (available from NIPRO CORPORATION), and naturalet (available from Arkray).

Next, at step S2, the skin 300 of the subject is cleaned by using an alcohol or the like to remove substances (sweat, dusts, etc.) that may be disturbance factors affecting measurement results. Thereafter, the flange 105 of the puncture device 100 to which the microneedle chip 200 is attached is placed on the skin 300 of the subject. Then, the release button 102 is pressed to cause the microneedles 201 of the microneedle chip 200 to come into contact with the skin 300 of the subject. In this manner, the micropores 301 are formed in the skin 300. The formation of the micropores prompts the extraction of a tissue fluid from the skin 300. According to these features, once the micropores are formed before the subject goes to bed, it is thereafter not necessary to prompt the extraction of the tissue fluid. Thus, unlike iontophoresis or the like, it is not necessary to apply a current when the subject is sleeping. This reduces influences on the sleep of the subject.

Subsequently, at step S3, the puncture device 100 is removed from the skin 300 of the subject. Thereafter, the holding sheet 11 of the collection member 10 is adhered to the skin 300 of the subject such that the collector 12 is placed at the area in which the micropores 301 have been formed (i.e., the micropore forming area). The subject timely goes to bed with the collection member 10 adhered to the skin. In this method, the subject is merely required to have the sheet-like member adhered to the skin. Therefore, the burden on the subject is greatly reduced as compared to conventional art in which the subject wears a device on his/her arm or a sensor is inserted in the skin. Moreover, rolling over or the like does not cause the collection member 10 to come off the skin of the subject. This assures the collection of the tissue fluid.

Next, after waking up, the subject removes the collection member 10 from the skin (step S4).

Thereafter, similar to step S1, the subject measures at step S5 the blood glucose level by a suitable method at a second time point (i.e., the measurement time t2), and records a measurement value BG2 (i.e., second blood glucose level information) and the measurement time t2.

Subsequently, at step S6, the subject operates the operation buttons 34 to input the measurement values BG1 and BG2 as well as the measurement times t1 and t2 into the diagnosis support apparatus 20.

Then, at step S7, the collection member 10 removed from the skin 300 of the subject is adhered to a predetermined position of the analysis cartridge 40, and the analysis cartridge 40 is placed at the cartridge placement part 22 of the diagnosis support apparatus 20.

Next, at step S8, the controller 35 performs a predetermined analysis process on the analysis cartridge 40 placed at the cartridge placement part 22.

In the above-described embodiment, the collection member 10 is removed at step S4; the blood glucose level information (BG2) is measured at step S5; and the measurement value BG2 is inputted at step S6. However, as an alternative, the subject first measures and inputs the blood glucose level information (BG2) after waking up, and then remove the collection member from the skin.

Figure 10:
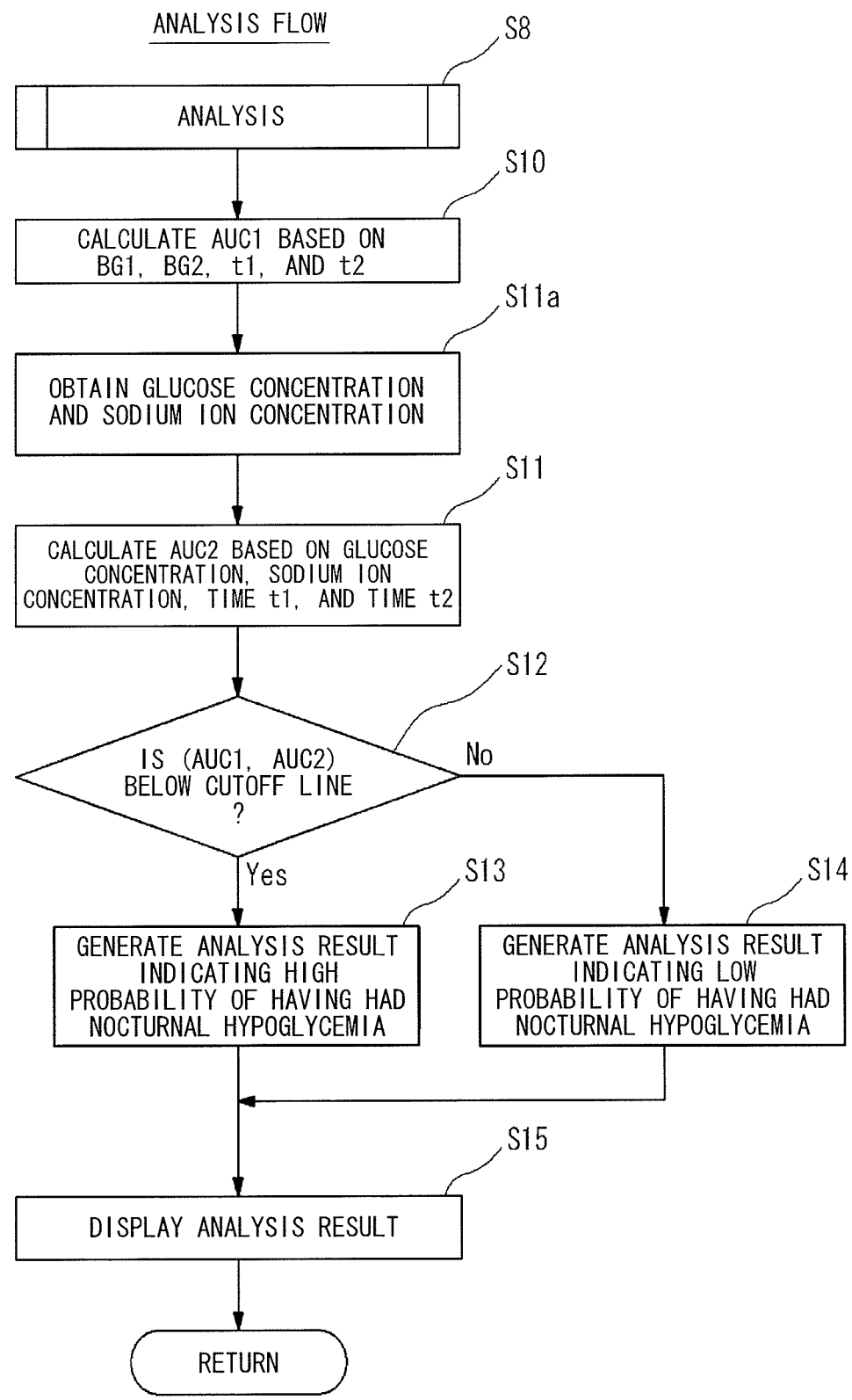
FIG. 10 is a flowchart showing a flow of an analysis process performed in the diagnosis support method of the present invention.

Next, the analysis process performed in the diagnosis support method will be described in detail. FIG. 10 is a flowchart showing a flow of processing by the controller 35 of the diagnosis support apparatus 20.

First, at step S10, the controller 35 calculates an area under the blood glucose-time curve AUC1 (i.e., a first integrated value) based on the measurement values BG1 and BG2 as well as the measurement times t1 and t2, which have been inputted at step S6.

Figure 11:
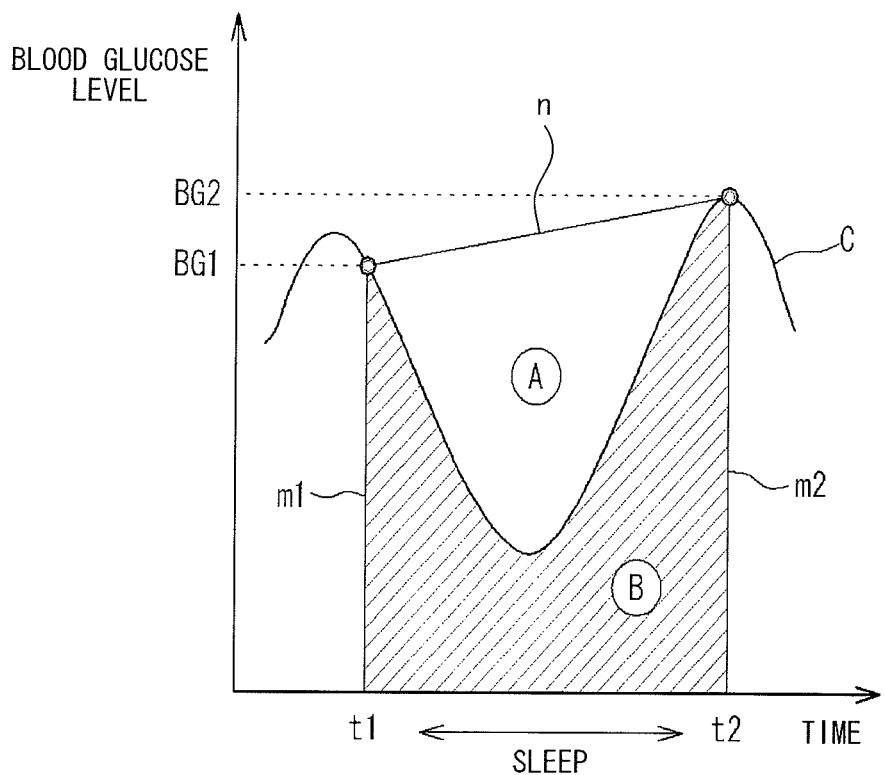
FIG. 11 is a blood glucose-time graph having an horizontal axis representing time and a vertical axis representing a blood glucose level.

As shown in FIG. 11, in the case of creating a blood glucose-time graph having a horizontal axis representing time and a vertical axis representing a blood glucose level, the AUC1 (i.e., the first integrated value) is the area of a trapezoid that is surrounded by a straight line m1, a straight line m2, a straight line n, and the time axis. The straight line m1 is perpendicular to the time axis and meets the first time point t1 indicated on the time axis; the straight line m2 is perpendicular to the time axis and meets the second time point t2 indicated on the time axis; the straight line n connects the blood glucose level BG1 at the first time point t1 and the blood glucose level BG2 at the second time point t2. It should be noted that if an actual blood glucose level has changed as indicated by a curve shown in FIG. 11, then the actual AUC is the area of a portion that is shown below the curve and above the time axis (i.e., the area of a hatched portion in FIG. 11).

Next, at step S11a, the controller 35 performs the above-described measurement process, thereby obtaining the glucose and sodium ion concentrations in the tissue fluid collected by the collection member 10.

Subsequently, at step S11, the controller 35 calculates an AUC2 (i.e., a second integrated value) by plugging the obtained glucose concentration Glc, the obtained sodium ion concentration Na, and an extraction period t (t2−t1) into an equation (1) below.

$$AUC2 = Glc \times vol / \{a \times (Na \times vol/t) + b\} \quad (1)$$

In the above equation, vol represents the volume of the collector (gel) 12, and a and b are constants obtained from an experiment.

The principle of AUC calculation based on the above equation (1) is described in detail in International Publication WO2010/013808. It should be noted that the disclosure of International Publication WO2010/013808 is incorporated herein by reference.

Hereinafter, the principle of the diagnosis support method of the present embodiment will be described.

As is clear from FIG. 11, the AUC1 is the area under the blood glucose-time curve under the assumption that the blood glucose level has linearly changed over a period from the first time point t1 to the second time point t2. In other words, the AUC1 is an ideal value of the area under the blood glucose-time curve in a case where the blood glucose level over a period from before the subject goes to bed until after the subject wakes up has changed in a simple manner without showing a valley-shaped curve.

On the other hand, generally speaking, an actual blood glucose level curve shows, as in FIG. 11, a valley-shaped curve over the period from the first time point t1 to the second time point t2. Thus, the value of an actual AUC deviates from the ideal value (i.e., deviates from the value of the AUC1). In the case of the subject having had nocturnal hypoglycemia, the blood glucose level curve of the subject shows a deeper valley than that shown by the blood glucose level curve of a healthy person. In this case, the actual AUC deviates from the AUC1 at a greater degree. Therefore, whether the probability of the subject having had nocturnal hypoglycemia is high or not can be estimated by obtaining the degree of deviation of the actual AUC from the AUC1 by comparing the actual AUC and the AUC1.

Accordingly, in the diagnosis support method of the present embodiment, an actual AUC (i.e., AUC2) is estimated based on the glucose concentration and the sodium ion concentration in the tissue fluid collected by the collector (gel). Then, the AUC1 and AUC2 are compared to estimate the probability of the subject having had nocturnal hypoglycemia. It has been verified that there is a high correlation between: the AUC that is calculated (estimated) based on the glucose and sodium ion concentrations in the tissue fluid extracted by means of the collector (gel) and the above equation (1); and an ACU that is obtained based on blood glucose levels that are obtained by actually collecting blood from the subject a plurality of times (see International Publication WO2010/013808).

It should be noted that the time t1 is a time point when the SMBG measurement is performed before the subject goes to bed, and the time t2 is a time point when the SMBG measurement is performed after the subject wakes up. That is, technically speaking, the period from t1 to t2 is different from the tissue fluid extraction period (i.e., the period during which the collection member is kept adhered to the skin) However, the period from the time t1 to a time at which the collection member is adhered to the skin, and the period from a time at which the collection member is removed from the skin to the time t2, are both approximately two to three minutes in general. Since these periods are insignificant as compared to the entire period (usually, approximately 7 to 8 hours) during which the collection member is kept adhered to the skin, there is substantially no influence on the calculation result of blood glucose AUC even if the aforementioned difference caused by these periods is ignored.

Next, at step S12, the controller 35 determines, in a coordinate system having a horizontal axis representing the AUC1 and a vertical axis representing the AUC2, whether a point representing the AUC1 calculated at step S10 and the AUC2 calculated at step S11 (AUC1, AUC2) is located below a cutoff line (i.e., a reference line) calculated in advance.

Figure 12:
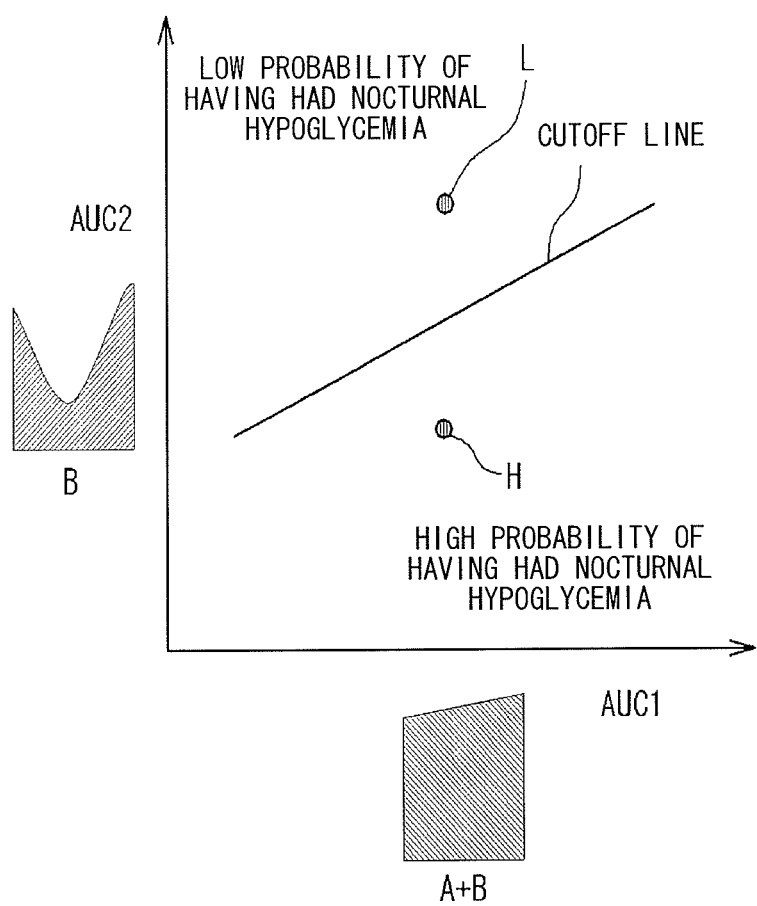
FIG. 12 shows an example of a cutoff line.

FIG. 12 shows an example of the cutoff line. In FIG. 12, a point denoted by H, at which the value of the AUC2 is smaller than that of the AUC1, is located below the cutoff line. This indicates that, during the period from the time t1 to the time t2 in FIG. 11, the blood glucose level dropped at a great degree (i.e., the blood glucose level curve shows a deep valley) and it is likely that the blood glucose level dropped to a level not higher than 70 mg/dl (i.e., presence of nocturnal hypoglycemia). On the other hand, in FIG. 12, a point denoted by L, at which the difference between the values of the AUC1 and AUC2 (AUC1-AUC2) is small, is located above the cutoff line. This indicates that, during the period from the time t1 to the time t2 in FIG. 11, the blood glucose level dropped at a small degree (i.e., the blood glucose level curve shows a shallow valley) and it is unlikely that the blood glucose level dropped to a level not higher than 70 mg/dl (i.e., absence of nocturnal hypoglycemia).

If the controller 35 determines that the point (AUC1, AUC2) is located below the cutoff line (reference line) calculated in advance (Yes at step S12), the controller 35 advances the processing to step S13. At step S13, the controller 35 generates diagnosis support information indicating that the subject is likely to have had nocturnal hypoglycemia. On the other hand, if the controller 35 determines that the point (AUC1, AUC2) is located above the cutoff line (reference line) calculated in advance (No at step S12), the controller 35 advances the processing to step S14. At step S14, the controller 35 generates diagnosis support information indicating that the subject is unlikely to have had nocturnal hypoglycemia.

Next, at step S15, the controller 35 causes the display 33 of the diagnosis support apparatus 20 to display: the diagnosis support information generated at step S13 (or S14), which indicates the high (or low) probability of the subject having had nocturnal hypoglycemia; the AUC1 calculated at step S10; and the AUC2 calculated at step S11.

<Setting of Cutoff Line>

Next, a method for setting the cutoff line used at step S12 will be described.

Figure 13:
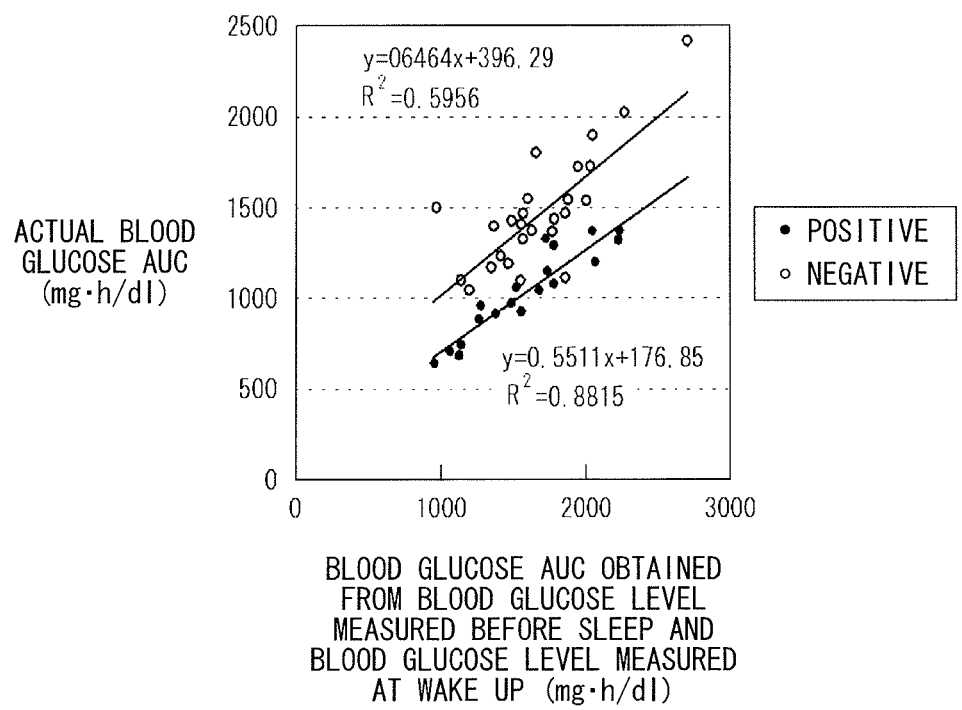
FIG. 13 shows blood glucose AUC analysis data regarding multiple subjects.

FIG. 13 shows analysis data that is obtained by analyzing temporal variation data regarding blood glucose levels obtained by a publicly-known conventional CGMS (Continuous Glucose Monitoring System) from multiple subjects.

The horizontal axis represents an ACU that is calculated, using the above-described AUC1 calculation method, based on the blood glucose level obtained by the CGMS at bedtime (22:00) and the blood glucose level obtained by the CGMS at wake-up time (08:00). The vertical axis represents an AUC that is obtained by integrating blood glucose levels obtained by the CGMS during the period from 22:00 to 08:00. In FIG. 13, the value of the horizontal axis corresponds to the AUC1, and the value of the vertical axis corresponds to the AUC2. In FIG. 13, black circles represent positive subjects who had nocturnal hypoglycemia and white circles represent negative subjects who did not have nocturnal hypoglycemia. A linear approximation equation where the AUC1 is x and the AUC2 is y can be obtained for each of the group of positive subjects and the group of negative subjects.

In the example of data shown in FIG. 13, the approximation equation for the positive group is an equation (2) shown below and the approximation equation for the negative group is an equation (3) shown below.

$$y=0.5511x+176.85 \tag{2}$$

$$(R^2=0.8815)$$

$$y=0.6464x+396.29 \tag{3}$$

$$(R^2=0.5956)$$

Figure 14:
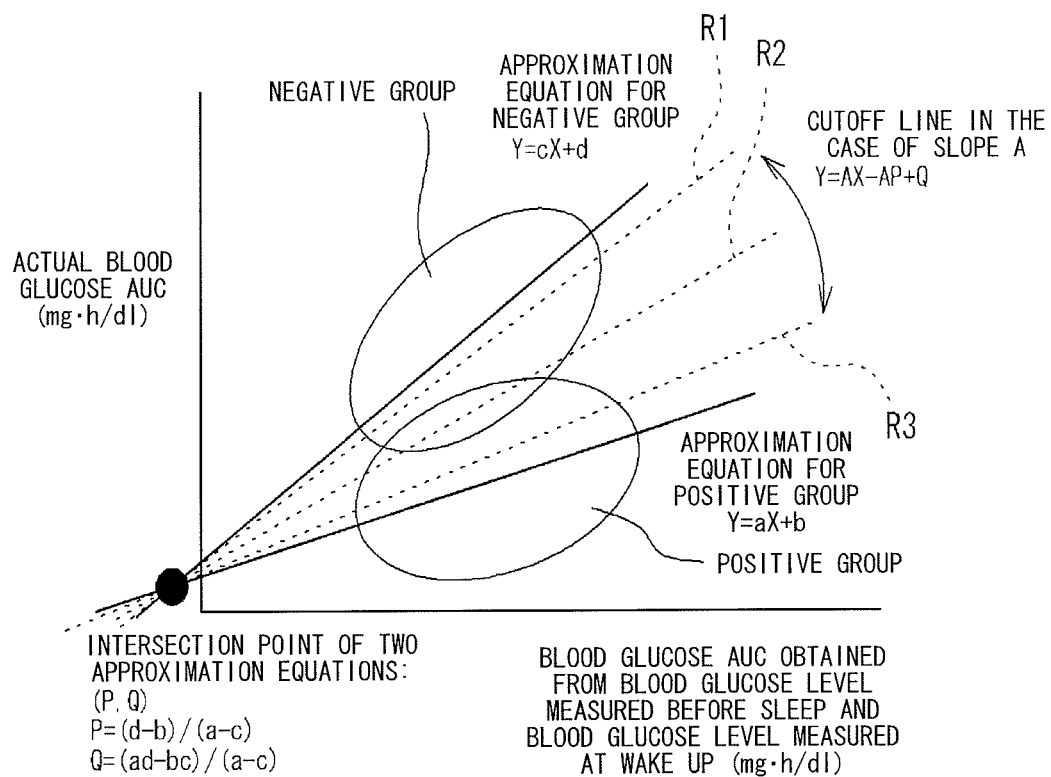
FIG. 14 illustrates the manner of obtaining a cutoff line.

The intersection point of these approximation equations (2) and (3) is as shown in FIG. 14.

If the approximation equation for the positive group is Y=aX+b and the approximation equation for the negative group is Y=cX+d, then the intersection point of the two approximation equations (P, Q) is represented as shown below.

$$P=(d-b)/(a-c)$$

$$Q=(ad-bc)/(a-c)$$

A straight line passing through the intersection point may be set as the cutoff line. The slope of the cutoff line may be changed depending on the objective of screening to be performed. If the slope is A, the cutoff line is represented by Y=AX−AP+Q.

The slope of the cutoff line determines the sensitivity and specificity of the screening. For example, among three cutoff lines shown in FIG. 14, the cutoff line R1 which has the steepest slope is a straight line passing above the positive group. This increases the probability of determining a subject who actually had nocturnal hypoglycemia (i.e., a positive patient) to be positive (i.e., determining that the subject is likely to have had nocturnal hypoglycemia). This, however, slightly increases the cases of determining a subject who did not have nocturnal hypoglycemia (i.e., a negative patient) to be positive (i.e., increased false positives). In other words, the sensitivity becomes closer to 100% but the specificity is slightly decreased. On the other hand, the cutoff line R3 which has the gentlest slope is a straight line passing below the negative group. This increases the probability of determining a subject who did not have nocturnal hypoglycemia (i.e., a negative patient) to be negative (i.e., determining that the subject is unlikely to have had nocturnal hypoglycemia). This, however, slightly increases the cases of determining a subject who had nocturnal hypoglycemia (i.e., a positive patient) to be negative (i.e., increased false negatives). In other words, the specificity becomes closer to 100% but the sensitivity is slightly decreased. The cutoff line R2 has a slope steeper than that of the cutoff line R3 and gentler than that of the cutoff line R1. Accordingly, the cutoff line R2 satisfies both the sensitivity and specificity to some extent.

[Other Variations]

The present invention is not limited to the above-described embodiment, and various modifications can be made.

For example, in the above embodiment, the blood glucose level is measured at the time t1 before the subject goes to bed and at the time t2 after the subject wakes up, and the AUC1 is calculated based on both the blood glucose levels. However, as an alternative, the AUC1 may be calculated based on one of the blood glucose level BG1 which is measured at the time t1 before the subject goes to bed and the blood glucose level BG2 which is measured at the time t2 after the subject wakes up.

Figure 15A:
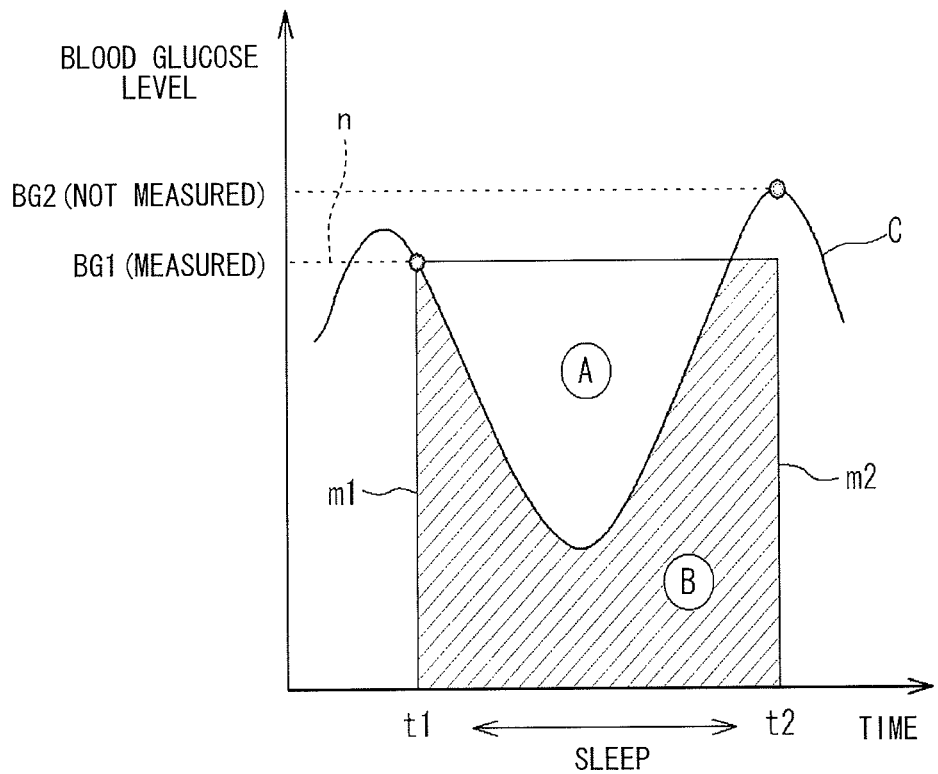
FIG. 15A is a schematic diagram of a case where an AUC 1 is calculated based on a single blood glucose level, which is a blood glucose level BG1 measured at a time t1 before bedtime.
Figure 15B:
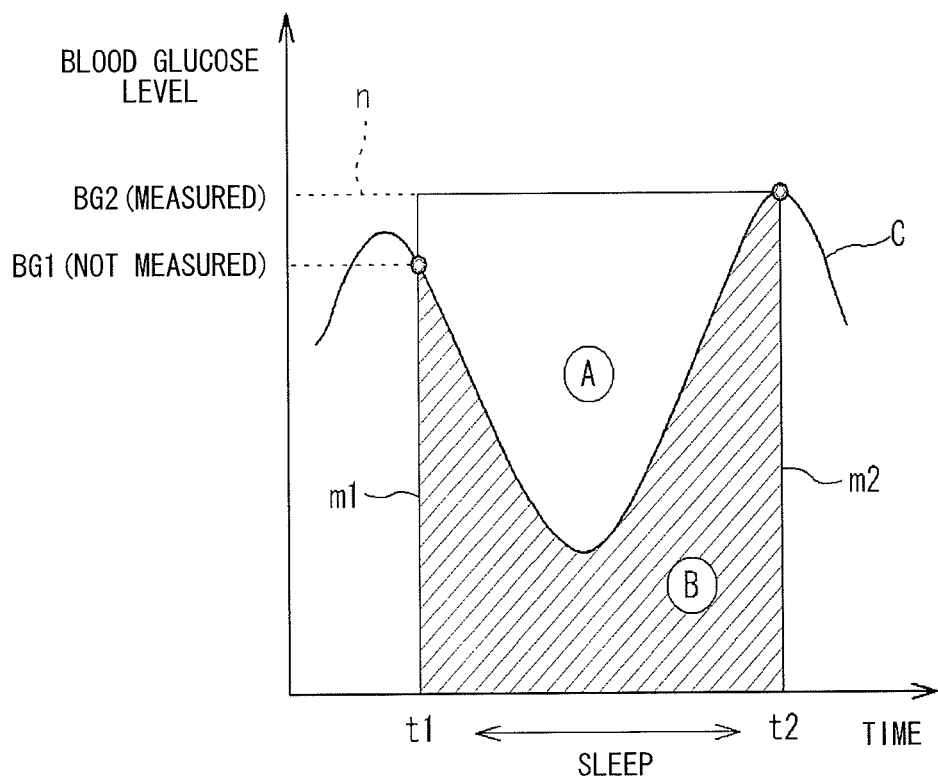
FIG. 15B is a schematic diagram of a case where the AUC 1 is calculated based on a single blood glucose level, which is a blood glucose level BG2 measured at a time t2 after wake-up time.

This variation is described below with reference to FIG. 15A and FIG. 15B. FIG. 15A is a schematic diagram of a case where the AUC1 is calculated based on a single blood glucose level, which is the blood glucose level BG1 measured at the time t1 before the subject goes to bed. FIG. 15B is a schematic diagram of a case where the AUC1 is calculated based on a single blood glucose level, which is the blood glucose level BG2 measured at the time t2 after the subject wakes up.

In the example of FIG. 15A, the AUC1 is the area of a rectangle that is surrounded by a straight line m1, a straight line m2, a straight line n, and the time axis. The straight line m1 is perpendicular to the time axis and meets the first time point t1 indicated on the time axis; the straight line m2 is perpendicular to the time axis and meets the second time point t2 indicated on the time axis; and the straight line n is parallel to the time axis and passes through the blood glucose level BG1 at the first time point t1. In this example, the blood glucose level BG2 at the second time point t2 is not measured. The second time point t2 is when the collection member 10 is removed.

In the example of FIG. 15B, the AUC1 is the area of a rectangle that is surrounded by a straight line m1, a straight line m2, a straight line n, and the time axis. The straight line m1 is perpendicular to the time axis and meets the first time point t1 indicated on the time axis; the straight line m2 is perpendicular to the time axis and meets the second time point t2 indicated on the time axis; and the straight line n is parallel to the time axis and passes through the blood glucose level BG2 at the second time point t2. In this example, the blood glucose level BG1 at the first time point t1 is not measured. The first time point t1 is when the collection member 10 is adhered to the skin.

If the AUC1 is calculated based on one of the blood glucose level BG1 which is measured at the time t1 before the subject goes to bed and the blood glucose level BG2 which is measured at the time t2 after the subject wakes up, then the number of times of measuring the blood glucose level is reduced. This reduces the number of times of collecting blood from the subject, thereby reducing the burden on the subject.

FIG. 16 shows analysis data that is obtained by analyzing temporal variation data regarding blood glucose levels obtained by a CGMS from multiple subjects, according to the above variation. The horizontal axis represents an AUC that is calculated by a method previously described with reference to FIG. 15A and that is calculated by using a single blood glucose level measured (at 22:00) before bedtime. Except that the horizontal axis is different, the manner of screening on multiple subjects is the same as that previously described with reference to FIG. 13. In this case, the sensitivity is 89% and the specificity is 96%. Thus, the screening is sufficiently effective even when the AUC is calculated based on a single blood glucose level measured before bedtime.

The above embodiment describes an example where hypoglycemia is evaluated based on the two axes that are: the AUC1 calculated from the blood glucose level BG1 measured before bedtime and the blood glucose level BG2 measured after wake-up time; and the AUC2. However, the present invention is not limited thereto. For example, hypoglycemia may be evaluated based on three axes of BG1, BG2, and AUC2.

Further, in the above embodiment, a cutoff line is set, which passes through the intersection point of the straight line that approximates the positive group and the straight line that approximates the negative group. Then, whether the probability of a subject having had nocturnal hypoglycemia is high or not is determined based on whether the point (AUC1, AUC2) is located above the cutoff line or below the cutoff line. However, the present invention is not limited thereto. For example, whether the probability of a subject having had nocturnal hypoglycemia is high or not may be determined based on whether the difference between the AUC1 and the AUC2 is greater than a predetermined threshold value or not. Alternatively, whether the probability of a subject having had nocturnal hypoglycemia is high or not may be determined based on whether the AUC2 divided by the AUC1 is greater than a predetermined threshold value or not.

Still further, in the above embodiment, the diagnosis support apparatus 20, which is a single apparatus, obtains the glucose concentration and the sodium ion concentration, calculates the AUC1 and the AUC2, and generates the diagnosis support information. However, as an alternative, an apparatus for obtaining the glucose concentration and the sodium ion concentration, an apparatus for calculating the AUC1 and the AUC2, and an apparatus for generating the diagnosis support information may be separately provided.

Still further, the above embodiment describes an example where the diagnosis support information about the presence or absence of nocturnal hypoglycemia is generated. However, according to the diagnosis support method of the present invention, a support can be provided for the diagnosis of the presence or absence of daytime hypoglycemia in addition to nocturnal hypoglycemia. Still further, the subject need not be entirely sleeping over the period from the first time point to the second time point during which the collection member is kept adhered to the skin. During the period, the subject may occasionally be awake.

What is claimed is:

1. A diagnosis support system comprising:
  a collection member configured to collect a tissue fluid from skin of a subject;
  a diagnosis support apparatus, wherein the diagnosis support apparatus comprises:
  a detector, located within the diagnosis support apparatus, and configured to obtain glucose information about an amount of glucose contained in the tissue fluid collected by the collection member which is placed on the skin of the subject for a predetermined period from a first time point to a second time point; and a controller, located within the diagnosis support apparatus, and a non-transitory memory programmed with instructions which cause the controller to perform an analysis process, wherein the analysis process includes:

- obtaining a first integrated value related to a glucose amount in the predetermined period, based on the first blood glucose level information and/or the second blood glucose level information and the predetermined period from the first time point to the second time point;
- obtaining a second integrated value related to a glucose amount in the body of the subject in the predetermined period from the first time point to the second time point, based on the glucose information; and
- generating diagnosis support information for supporting a diagnosis of presence or absence of hypoglycemia in the subject, based on the first integrated value and second integrated value.

2. The system of claim 1, wherein the analysis process includes obtaining the first integrated value based on the first blood glucose level information and the second blood glucose level information, and the first integrated value is an area of a region in a blood glucose level-time graph, which region is surrounded by a straight line that is perpendicular to a time axis and that meets the first time point indicated on the time axis, a straight line that is perpendicular to the time axis and that meets the second time point indicated on the time axis; a straight line that connects the blood glucose level at the first time point and the blood glucose level at the second time point, and the time axis.

3. The system of claim 1, wherein the second integrated value is calculated based on a concentration of the glucose contained in the tissue fluid collected by the collection member.

4. The system of claim 1, wherein the analysis process includes outputting the diagnosis support information based on the first integrated value, the second integrated value, and a predetermined condition.

5. The system of claim 4, wherein the predetermined condition is a predetermined threshold value, and the analysis process includes generating the diagnosis support information based on the predetermined threshold value and a value that is obtained based on the first integrated value and the second integrated value.

6. The system of claim 5, wherein the predetermined threshold value is obtained based on the first integrated value and the second integrated value, which are obtained from a subject in whom the presence or absence of hypoglycemia is known.

7. The system of claim 1, further comprising;

a micropore forming device for forming micropores in the skin of the subject.

8. The system of claim 1, wherein the first time point is before a bedtime when the subject goes to bed; and the second time point is after a wake-up time when the subject wakes up.

9. A diagnosis support apparatus comprising:

a detector configured to obtain glucose information about an amount of glucose contained in a tissue fluid collected by a collection member which is placed on skin of a subject for a predetermined period from a first time point to a second time point;

a controller, located within the diagnosis support apparatus, and a non-transitory memory programmed with instructions which cause the controller to perform an analysis process, wherein the analysis process includes;

- obtaining a first integrated value related to a glucose amount in the predetermined period, based on the first blood glucose level information and/or the second blood glucose level information and the predetermined period from the first time point to the second time point;
- obtaining a second integrated value related to a glucose amount in the body of the subject in the predetermined period from the first time point to the second time point, based on the glucose information; and
- generating diagnosis support information for supporting a diagnosis of presence or absence of hypoglycemia in the subject, based on the first integrated value and the second integrated value.

10. The system of claim 1, wherein the first blood glucose level information is information about the blood glucose level of the subject before the bedtime of the subject, the second blood glucose level information is information about the blood glucose level of the subject after the wake-up time of the subject, obtaining glucose information is obtaining information about an amount of the glucose contained in the tissue fluid collected by the collection member which is placed on the skin of the subject for a period that starts before the bedtime of the subject and ends after the wake-up time of the subject.

11. The system of claim 1, comprising an operation part for inputting the first blood glucose level information, the second blood glucose level information, and the glucose information.

12. The apparatus of claim 9, comprising an operation part for inputting the first blood glucose level information, the second blood glucose level information, and the glucose information.

13. The system of claim 1, wherein the collection member is a gel.

14. The apparatus of claim 9, wherein the collection member is a gel.

* * * * *